United States Patent [19]

Farng et al.

[11] Patent Number: 4,966,721

[45] Date of Patent: Oct. 30, 1990

[54] N-N'-DIHYDROCARBYL SUBSTITUTED PHENYLENE DIAMINE-DERIVED CONDENSATION PRODUCTS AS ANTIOXIDANTS AND LUBRICANT COMPOSITIONS

[75] Inventors: Liehpao O. Farng, Lawrenceville; Andrew G. Horodysky, Cherry Hill, both of N.J.

[73] Assignee: Mobil Oil Corporation, Fairfax, Va.

[21] Appl. No.: 381,890

[22] Filed: Jul. 19, 1989

[51] Int. Cl.$^5$ .......................................... C10M 133/12
[52] U.S. Cl. ............................... 252/51.5 R; 564/305; 564/306; 252/401
[58] Field of Search ......................... 252/51.5 R, 401; 564/305, 306

[56] References Cited

U.S. PATENT DOCUMENTS

| | | | |
|---|---|---|---|
| 2,361,391 | 10/1944 | Fraser et al. | 252/51.5 R |
| 2,432,713 | 12/1947 | Bartleson | 252/51.5 R |
| 3,189,650 | 6/1965 | Chenicek | 252/51.5 R |
| 3,238,177 | 3/1966 | Chenicek | 252/51.5 R |
| 3,623,984 | 11/1971 | Carlos et al. | 252/51.5 R |
| 4,202,782 | 5/1980 | Doe, Jr. et al. | 252/51.5 R |

*Primary Examiner*—Jacqueline V. Howard
*Attorney, Agent, or Firm*—A. J. McKillop; C. J. Speciale; H. M. Flournoy

[57] ABSTRACT

N-N'-dihydrocarbyl substituted phenylenediamine-derived Mannich-type condensation products are effective antioxidants for lubricants.

60 Claims, No Drawings

N-N'-DIHYDROCARBYL SUBSTITUTED PHENYLENE DIAMINE-DERIVED CONDENSATION PRODUCTS AS ANTIOXIDANTS AND LUBRICANT COMPOSITIONS

BACKGROUND OF THE INVENTION

The present invention relates to compositions of matter comprising dihydrocarbyl substituted phenylenediamine derived condensation products and to lubricant compositions containing small additive amounts thereof.

Lubricants, such as lubricating oils and greases, are subject to oxidative deterioration at elevated temperatures or upon prolonged exposure to the elements. Such deterioration is evidenced, in many instances, by an increase in acidity and in viscosity, and when the deterioration is severe enough, it can cause metal parts to corrode. Additionally, severe oxidation leads to a loss of lubrication properties, and in especially severe cases this may cause complete breakdown of the device being lubricated. Many additives have been tried, however, many of them are only marginally effective except at high concentrations. Improved antioxidants are clearly needed.

Antioxidants or oxidation inhibitors are used to minimize the effects of oil deterioration that occur when hot oil is contacted with air. The degree and rate of oxidation will depend on temperature, air and oil flow rates and, of particular importance, on the presence of metals that may catalytically promote oxidation. Antioxidants generally function by prevention of chain peroxide reaction and/or metal catalyst deactivation. They prevent the formation of acid sludges, darkening of the oil and increases in viscosity due to the formation of polymeric materials.

Water (moisture) is another critical problem. In spite of even extraordinary precautionary efforts water is found as a film or in minute droplets in vessels containing various hydrocarbon distillates. This brings about ideal conditions for corrosion and damage of metal surfaces of the vessels and the materials contained therein. Also in the lubrication of internal combustion engines, for example, quantities of water are often present as a separate phase within the lubricating system. Another serious problem in respect to metallic surfaces in contact with adjacent metallic surfaces is the surface wear caused by the contact of such surfaces. One material capable of simultaneously effectively coping with such problems as these is highly desireous.

It has now been found that the use of dihydrocarbyl substituted phenylenediamines provides exceptional antioxidant activity. These remarkable benefits are to be expected for a variety of synthetic and mineral oil based lubricants.

To the best of our knowledge, these compositions have not been previously used as additives in lubricating oils or greases. The additive products themselves and lubricant compositions thereof are both believed to be novel.

The use of arylamines, such as phenylenediamines, diphenyl amines, phenyl alpha-naphthylamines, as antioxidants has been well known in a variety of lubricant, polymer and rubber applications.

The use of aliphatic amine derivatives has been widely reported as having beneficial multifunctional detergency, dispersancy, and stabilizing properties.

It has now been found that the use of these phenylene diamine/aldehyde-(ketone)/alkylamine-derived condensation products provides exceptional antioxidant activity with potential detergency, and high temperature stabilizing properties.

It is an object of this invention to provide lubricant compositions of improved antioxidant characteristics. It is a further object to provide novel additives derived from the hereinbelow described Mannich condensation products.

SUMMARY OF THE INVENTION

This application is directed to lubricant compositions containing small concentrations of dihydrocarbyl substituted phenylenediamine-aldehyde(ketone)-alkyl amine condensation products which possess excellent antioxidant properties. Both the pheneylenedimaine moiety and the aliphatic amine moiety are believed to provide the basis for the synergistic antioxidant activity each of which is subsequently enhanced by the integral alkyl coupling moiety (CRR' group derived from ketones or aldehydes CRR''=0). The aliphatic amine group is believed to contribute additional detergency/dispersancy properties to these novel additives. Both the arylamine and alkylamine moieties may additionally contribue significant metal deactivating properties to this new class of additives.

Although applicants do not wish to be limited to a particular theory, all of these beneficial properties are believed to enhanced to as as a result of this novel internal synergism. This unique internal synergism concept is believed to be applicable to similar structures containing (a) phenylene diamine groups, (b) aliphatic amine groups, and (c) substituted or non-substituted methylene linkages within the same molecule. The products of this patent application show good stability and compatibility when used in the presence of other commonly used additives in lubricant compositions.

DESCRIPTION OF PREFERRED EMBODIMENTS

Generally speaking, the products in accordance with the invention are prepared as described below.

N,N'-dihydrocarbyl substituted para-phenylenediamine (A, commerically available from Uniroyal Chemical Company) was reacted with an aldehyde (or ketone), and an aliphatic amine to form the Mannich-type condensation products in accordance with the invention and as described in Equation 1.

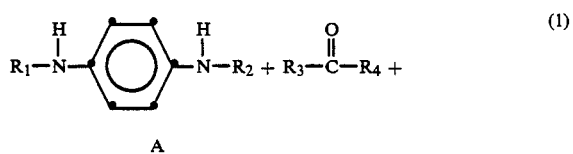

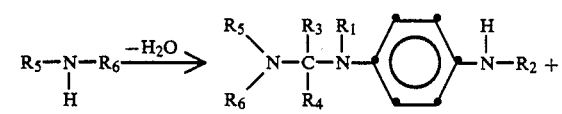

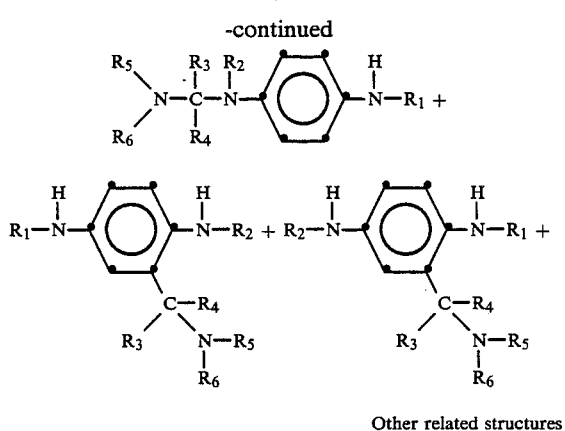

Other related structures where $R_1$, $R_2$, $R_3$, $R_4$, $R_5$, $R_6$ are hydrogen or $C_1$ to $C_{60}$ hydrocarbyl or oxygen, sulfur or nitrogen containing $C_2$ to about $C_{60}$ hydrocarbyl.

Other phenylenediamines, such as monosubstituted para-phenylenediamine (B), mono- and di-substituted meta-phenylenediamine (C and D), mono- and di-substituted ortho-phenylenediamine (E and F) are also suitable for conducting similar reactions as in Eqauation 1.

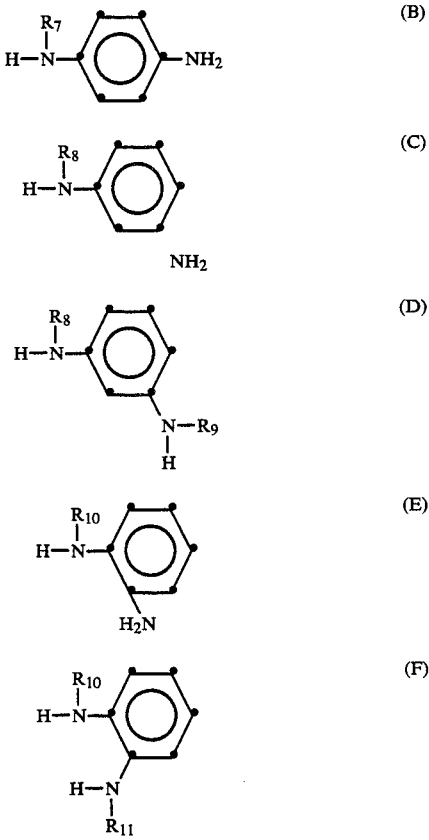

Where $R_7$, $R_8$, $R_9$, $R_{10}$, and $R_{11}$ are $C_1$ to $C_{60}$ hydrocarbyl or oxygen, sulfur or nitrogen containg $C_2$ to about $C_{60}$ hydrocarbyl.

Any suitable phenylenediamine may be used herein. However, the preferred phenylenediamines include N,N'-bis(1,4-dimethylpentyl)] meta-phenylenediamine, N,N'-bis (1,4-dimethylpentyl) para-phenylenediamine and N,N'-di-sec-butyl para-phenylenediamine and the like.

Any suitable aldehyde or ketone may be used herein. Especially preferred are formaldehyde, paraformaldehyde and 2-ethylhexanal and the like. Therefore, less than molar, molar or more than molar amounts of either amine or diamine may be used. Although stoichiometric amounts of amine may on occasion be preferred, an excess, or less than stoichiometric amounts can often be used. Thus an excess of one reagent or another can be used.

Any suitable hydrocarbyl amine may be used herein. Preferred amines include bis(2-ethylhexyl) amine, diethanolamine, polyether amines, Primene 81R (a commercial mixture of $C_{11}$–$C_{14}$ tertiary alkyl primary amines). The polyether amines include polyoxyalkyleneamines, polyoxyalkylenediamines, polyoxyalkylenetriamines, (Jeffamine M, D and T series based on propylene oxides (PO), ethylene oxide, (EO) or mixed EO/PO polyether backbones, or any other suitable alkylene oxide derived polyether backbones.) The hydrophobic hydrocarbons can be straight-chain alkyl or arylalkyl or alkylaryl hydrocarbyl. One highly suitable polyether amine is Surfonamide MNPA (Texaco), a primary polyether amine derived from nonylphenol (alkylaryl) and EO/PO polyether backbones.

Generally speaking the various reaction parameters, i.e., times, temperatures pressures and quantities of reactive materials may vary widely and are not believed to be critical. However, the temperature may vary from ambient or about 50° C. to about 25° C. at pressures from atmospheric to slightly higher with reaction times from about one hour or less also at 24 hours or more.

The additives may be incorporated into any suitable lubricating media which comprises oils of lubricating viscosity, e.g., mineral or synthetic; or mixtures of mineral and synthetic or greases in which the aforementioned oils are employed as a vehicle or into such functional fluids as hydraulic fluids, brake fluids, power tranmsission fluids and the like. In general, mineral oils and/or synthetic, employed as the lubricant oil, or grease vehicle may be of any suitable lubricating viscosiy range, as for example, from about 45 SSU at 100° F. to about 6000 SSU at 100° F., and, preferably, from about 50 to about 250 SSU at 210° F. These oils may have viscosity indices from below zero to about 100 or higher. Viscosity indices from about 70 to about 95 are preferred. The average molecular weight of these oils may range from about 250 to about 800. Where the lubricant is to be employed in the form of a grease, the lubricating oil is generally employed in an amount sufficient to balance the total grease composition, after accounting for the desired quantity of the thickening agent and other additive components to be included in the grease formulation.

In instances where synthetic oil, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylolpropane esters, neopentyl and pentaerythritol esters, di(2-ethylhexyl) sebacate, di(2-ethylhexyl) adipate, dibutyl phthalate, fluorocarbons, silicate esters, silanes, esters or phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers, etc.

Fully formulated lubricating oils may include a variety of additives (for their known purpose) such as dispersants, detergents, inhibitors, antiwear agents, extreme pressure additives, antioxidant, antifoam, pour depressant and other additives including metallic or non-metallic phenates, sulfonates, succimides, esters, amides, sulfurized olefins, and zinc dithiophosphates.

As hereinbefore indicated, the aforementioned additive compounds may be incorporated as multifunctional agents in grease compositions. When high temperature stability is not a requirement of the finished grease, mineral oils having a viscosity of at least 40 SSU at 150° F., and particularly those falling within the range from about 60 SSU to about 6,000 SSU at 100° F. may be employed. The lubricating vehicles of the improved greases of the present invention, containing the above described additives, are combined with a grease forming quantity of a thickening agent. For this purpose, a wide variety of materials dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickners may be employed which do not melt and dissolve when used at the required temperature within a particular environment; soap thickeners such as metallic (lithium or calcium) soaps including hydroxy stearate and/or stearate soaps can be used however, in all other respects, any material which is normally employed for thickening or gelling hydrocarbon fluids or forming greases can be used in preparing the aforementioned improved greases in accordance with the present invention.

Included among the preferred thickening agents are those containing at least a portion of alkali metal, alkaline earth metal or amine soaps of hydroxyl-containing fatty acids, fatty glycerides and fatty esters having from 12 to about 30 carbon atoms per molecule. The metals are typified by sodium, lithium, calcium and barium. Preferred is lithium. Preferred members among these acids and fatty materials are 12-hydroxystearic acid and glycerides containing 12-hydroxystearates, 14-hydroxystearic acid, 16-hydroxystearic acid and 6-hydroxystearic acid.

The reaction products are highly useful as multifunctional antioxidant/anticorrosion agents. They are added to the lubricating medium in amounts sufficient to impart such properties to the lubricant. More particularly, such properties will be imparted to the lubricant by adding from about 0.001% to about 10% by weight, preferably from about 0.01% to about 3%, of the neat product.

The following examples are exemplary only and are not intended as limitations.

EXAMPLE 1

Approximately 76.4 grams of commercial Primene 81R (Rohm & Haas), and 122.4 grams N,N'-bis(1,4-dimethylpentyl) para-phenylenediamine (commercially available from Uniroyal Chemical Company under the trade name Naugalube 443) were mixed in a rector equipped with a heater, an agitator, and a Dean-Stark tube with condenser. The reactants were heated at 50° C., and 12.6 grams of paraformaldehyde was added in four portions over a course of an hour. Thereafter, this mixture was heated at 100° C. for one hour, at 120° C. for another five hours during which 5.5 grams of water was collected in the Dean-Stark condenser. Finally, the solution was filtered through diatomaceous earth to produce a dark fluid as the desired product.

EXAMPLE 2

Approximately 42 grams of diethanolamine (0.4 mole), and 122.4 grams of N,N'-bis(1,4-dimethylpentyl) para-phenylenediamine (Naugalube 443 from Uniroyal, 0.4 mole) were charged in a four-neck flask. Slowly, 51.3 grams of 2-ethylhexanal (0.4 mole) was added dropwise from a dropping funnel at 60° C. over a course of one hour. Thereafter, the reactants were heated at 100° C. for an hour, and at 120° C. for three hours. The volatiles were removed by vacuum distillation and the product was filtered through diatomaceous earth.

EXAMPLE 3

Approximately 72.3 grams of bis(2-ethyhexyl) amine, 55 ml of methanol and 25.0 grams of aqueous formaldehyde (37 weight percent solution, 0.308 mole) were charged in a four-neck flask, and the reactants were stirred at 45° to 50° C. for 15 minutes. Then 91.8 grams of N,N'-bis(1,4-dimethylpentyl) para-phenylenediamine (Naugalube 443) was added and the mixture was heated to 75° C. and held for three hours. Thereafter, the reaction temperature was gradually increased from 75° C. to 110° C. and was held at 110° C. for two additional hours, while removing methanol and water from the Dean-Stark condenser. Approximately 169 grams of the desired product was isolated.

EXAMPLE 4

Approximately 114 grams of alkylphenol derived polyether amine (commercial chemical from Texaco Chemical Company, under the trade name Surfonamine MNPA 380), 60 ml methanol and 25 grams of aqueous formaldehyde (37 weight percent solution, 0.308 mole) were charged in a flask, and the reactants were reacted at 50° C. for 15 minutes. Approximately 66 grams of N,N'-di-sec-butyl para-phenylenediamine (Naugalube 403 from Uniroyal Chemical Company) was added, and the mixture was refluxed at the boiling point of methanol over a course of three hours. Thereafter, the reaction temperature was gradually increased from 75° C. to 110° C., while removing volatiles through the condenser. Two additional hours of heating produced no more water of reaction. The final product is a dark liquid weighing 182.4 grams.

Evaluation of the Products

The phenylenediamine derived condensation products were blended into mineral oils and evaluated for antioxidant performance by the Catalytic Oxidation Test at 325° F. for 40 hours (Table 1); Catalytic Oxidation Test at 325° F. for 72 hours (Table 2). A comparison of the oxidation-inhibiting characteristics of the inventive products with traditional antioxidants in the same mineral oils is also included in Table 1 and 2.

Catalytic Oxidation Test

The test lubricant composition is subjected to a stream of air which is bubbled through the composition at a rate of 5 liters per hour at the specified temperature for the required number of hours. Present in the composition (comprising a 200 second solvent refined paraffinic neutral oil) in addition to the additive compound were metals commonly used as materials to construct engines namely:
(a) 15.6 square inch of sand-blasted iron wire;
(b) 0.78 square inch of polished copper wire;
(c) 0.87 square inch of polished aluminum wire; and
(d) 0.107 square inch of polished lead surface.

As noted above, the test results are reported in Tables 1 and 2.

TABLE 1

Catalytic Oxidation Test
10 Hours at 325° F.

| Item | Additive Conc. (Wt %) | Change In Acid Number $\Delta$ TAN | Percent Change In Viscosity $\Delta$ KV, % | Lead Loss, Mg |
|---|---|---|---|---|
| Base Oil (200 second, solvent refined, paraffinic neutral, mineral oil) | — | 4.78 | 57.9 | 2.9 |
| Example 1 in above base oil | 1.0 | 0.00 | 4.5 | 0.0 |
| Example 2 in above base oil | 1.0 | 0.51 | 10.7 | 0.8 |
| Example 3 in above base oil | 1.0 | 0.18 | 2.0 | 0.2 |
| Example 4 in above base oil | 1.0 | 0.17 | 1.7 | 0.3 |
| Prior Art Antioxidants | | | | |
| Arylamine Antioxidant (Irganox L-57)* | 1.0 | 1.26 | 11.2 | 0.0 |
| Phenolic Antioxidant (Irganox L-130)* | 1.0 | 5.31 | 45.1 | 0.0 |
| 4,4'-Methylene bis(2,6-di-t-butyl) phenol | 1.0 | 6.24 | 62.4 | 0.0 |

*Ciba Geigy product

TABLE 2

Catalytic Oxidation Test
72 Hours at 325° F.

| Item | Additive Conc. (Wt %) | Change In Acid Number $\Delta$ TAN | Percent Change In Viscosity $\Delta$ KV, % | Lead Loss, Mg |
|---|---|---|---|---|
| Base Oil (200 second, solvent refined, paraffinic neutral, mineral oil) | — | 8.53 | 99.4 | 5.2 |
| Example 1 in above base oil | 1.0 | 0.22 | 8.1 | 0.0 |
| Example 2 in above base oil | 1.0 | 0.26 | 6.7 | 0.2 |
| Example 3 in above base oil | 1.0 | 0.32 | 5.1 | 0.2 |
| Prior Art Antioxidants | | | | |
| Phenolic Antioxidant (Irganox L-130)* | 1.0 | 6.48 | 58.1 | 0.0 |
| 4,4'-Methylene bis(2,6-di-t-butyl) phenol | 1.0 | 7.13 | 101.3 | 0.0 |
| Arylamine Antioxidant (Irganox L-57)* | 1.0 | 6.14 | 79.1 | 0.0 |

*Ciba Geigy product

As can be seen from the Table 1 and Table 2 test results, the products show very good antioxidant activity as evidenced by control of increase in acidity, viscosity and lead loss, and clearly out-perform the traditional commercially used phenolic and arylamine antioxidants.

The products of Example 1, 2, 4, and 3 were also blended into the same mineral oils for copper strip corrosivity test (Table 3), ASTM D-130. Further details may be found in *ASTM Standards on Petroleum Products and Lubricants*, published annually the American Society for Testing Materials. The resultrs were excellent and show no deleterious effect on corrosivity to the base oils.

TABLE 3

| (D130) Copper Strip Corrosivity Test (250° F., Hours) | | |
|---|---|---|
| Item | Additive Conc. (Wt. %) | Corosivity Rating |
| Base Oil (200 second, solvent refined, paraffinic neutral, mineral oil) | — | 1A |
| Example 1 in above base oil | 1.0 | 1A |
| Example 2 in above base oil | 1.0 | 1A |
| Example 3 in above base oil | 1.0 | 1A |
| Example 4 in above base oil | 1.0 | 1A |

Corrosivity Test rating: 1 for slight tarnish, 2 for moderate tarnish, 3 for dark tarnish and 4 for corrosion.

As shown above, the products of this invention exhibit very good antioxidant activity, especially under the very severe conditions shown in Table 2. The products of this invention when used in premium quality automotive and industrial lubricants will significantly enhance the stability and extend the service life of the lubricant. These novel compositions described in this patent application are useful at low concentrations and do not contain any potential undesirable metals or chlorine or phosphorus. These multifunctional antioxidants can be commercially made using known technology in existing equipment.

Although the present invention has been described with preferred embodiments, it is to be understood that modifications and variations may be utilized without departing from the spirit and scope of this invention, as those skilled in the art will readily understood. Such modifications and variations are considered to be within the purview and scope of the appended claims.

What is claimed is:

1. A composition comprising a major amount of an oil of lubricating viscosity or grease or other solid lubricant prepared therefrom and a minor multifunctional antioxidant/corrosion inhibiting amount of the product of reaction of (1) a N,N-dihydrocarbyl substituted phenylenediamine having the following generalized structure:

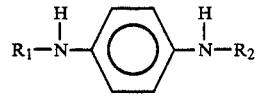

(2) an aldehyde or ketone having the following generalized structure:

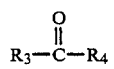

and (3) an aliphatic amine having the following generalized structure:

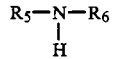

where $R_1$, $R_2$, $R_3$, $R_4$, $R_5$, $R_6$ are hydrogen or $C_1$ to $C_{60}$ hydrocarbyl, or oxygen, sulfur, nitrogen containing $C_2$ to about $C_{60}$ hydrocarbyl or mixtures thereof.

2. The composition of claim 1 where the product has at least one structure having the following generalized formula:

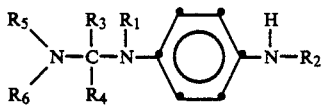

where $R_1$, $R_2$, $R_3$, $R_4$, $R_5$ and $R_6$ are hydrogen or $C_1$ to about $C_{60}$ hydrocarbyl, or $C_1$ to $C_{60}$ hydrocarbyl, or oxygen, sulfur, nitrogen containing $C_2$ to about $C_{60}$ hydrocarbyl or mixtures thereof.

3. The composition of claim 1 where the product comprises at least one structure having the following generalized formula:

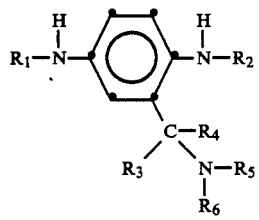

where $R_1$, $R_2$, $R_3$, $R_4$, $R_5$ and $R_6$ are hydrogen or $C_1$ to about $C_{60}$ hydrocarbyl, or $C_1$ to $C_{60}$ hydrocarbyl, or oxygen, sulfur, nitrogen containing $C_2$ to about $C_{60}$ hydrocarbyl or mixtures thereof.

4. The composition of claim 1 where the product comprises at least one structure having the following generalized formula:

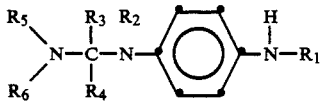

where $R_1$, $R_2$, $R_3$, $R_4$, $R_5$ and $R_6$ are hydrogen or $C_1$ to about $C_{60}$ hydrocarbyl, or $C_1$ to $C_{60}$ hydrocarbyl, or oxygen, sulfur, nitrogen containing $C_2$ to about $C_{60}$ hydrocarbyl or mixtures thereof.

5. The composition of claim 1 where the product comprises at least one structure having the following generalized formula:

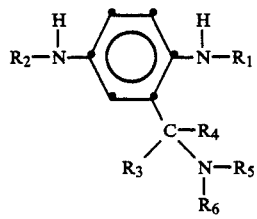

where $R_1$, $R_2$, $R_3$, $R_4$, $R_5$ and $R_6$ are hydrogen or $C_1$ to about $C_{60}$ hydrocarbyl, or $C_1$ to $C_{60}$ hydrocarbyl, or oxygen, sulfur, nitrogen containing $C_2$ to about $C_{60}$ hydrocarbyl or mixtures thereof.

6. The composition of claim 1 where the phenylenediamine is selected from the group consisting of mono- and di-substituted para-phenylenediamines, mono- and di-substituted meta-phenylenediamines, and mono- and di-substituted ortho phenylenediamines.

7. The composition of claim 6 where the phenylenediamine has the following generalized structure

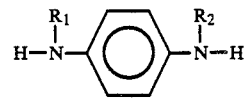

where $R_1$, $R_2$ and $C_1$ to about $C_{60}$ hydrocarbyl or oxygen, sulfur or nitrogen containing $C_2$ to about $C_{60}$ hydrocarbyl.

8. The composition of claim 6 where the phenylenediamine has the following generalized structure:

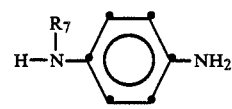

where $R_7$ is $C_1$ to about $C_{60}$ hydrocarbyl or oxygen, sulfur or nitrogen containing $C_2$ to about $C_{60}$ hydrocarbyl.

9. The composition of claim 6 where the phenylenediamine has the following generalized structure:

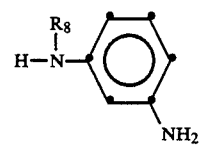

where $R_8$ is $C_1$ to about $C_{60}$ hydrocarbyl or oxygen, sulfur or nitrogen containing $C_2$ to about $C_{60}$ hydrocarbyl.

10. The composition of claim 6 where the phenylenediamine has the following generalized structure:

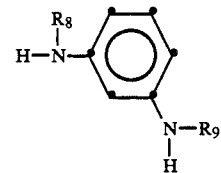

where $R_8$ and $R_9$ are $C_1$ to about $C_{60}$ hydrocarbyl or oxygen, sulfur or nitrogen containing $C_2$ to about $C_{60}$ hydrocarbyl.

11. The composition of claim 6 where the phenylenediamine has the following generalized structure:

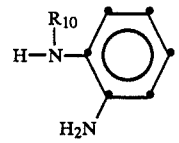

where $R_{10}$ is $C_1$ to about $C_{60}$ hydrocarbyl or oxygen, sulfur or nitrogen containing $C_2$ to about $C_{60}$ hydrocarbyl.

12. The composition of claim 6 where the phenylenediamine has the following generalized structure:

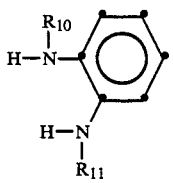

where $R_{10}$ and $R_{11}$ are $C_1$ to about $C_{60}$ hydrocarbyl or oxygen, sulfur or nitrogen containing $C_2$ to about $C_{60}$ hydrocarbyl.

13. The composition of claim 1 wherein said reaction is carried out with less than molar, molar and more than molar quantities of either amine or phenylenediamine.

14. The composition of claim 1 where the reactants are a mixture of $C_{11}$–$C_{14}$ tertiary-alkyl amines, N,N'-bis(1,4-dimetylpentyl) para-phenylenediamine and para-formaldehyde.

15. The composition of claim 1 where the reactants are a mixture of diethanol amine, N,N'-bis(1,4-dimethylpentyl) para-phenylenediamine and 2-ethylhexanal.

16. The composition of claim 1 where the reactants are a mixture of bis(2-ethyhexyl) amine, formaldehyde and N,N'-bis(1,4-dimethylphentyl) para-phenylenediamine.

17. The composition of claim 1 where the reactants are a mixture of a polyether amine, formaldehyde and N,N'-di-sec-butyl-para-phenylene diamine.

18. The composition of claim 17 where the polyether amine is selected from polyoxyalkyleneamines, polyoxyalkylenediamines and polyoxy alkylenetriamines.

19. The composition of claim 17 where the polyether amine is selected from propylene oxide ethylene oxide or mixed propylene oxides/ethylene oxide based polyether amines.

20. The composition of claim 19, where the polyether amine is a primary polyether amine derived from nonylphenol and ethylene oxide propylene oxide backbones.

21. The composition of claim 20 where the polyether amine is Surfonamine MNPA.

22. The composition of claim 1 where said oil of lubricating viscosity is selected from mineral oils, synthetic oils and mixtures thereof.

23. The composition of claim 22 where said oil is a mineral oil.

24. The composition of claim 22 where said oil is a synthetic oil.

25. The composition of claim 22 where said oil is a mixture of synthetic and mineral oil.

26. The composition of claim 1 where said composition is a grease composition.

27. The composition of claim 1 comprising from about 0.001 to 10 weight percent based on the total weight of the composition of said condensation product.

28. The composition of claim 27 comprising from about 0.01 to 3 weight percent based on the total weight of the composition of said condensation product.

29. A product of reaction made by reacting (1) a N,N'-dihydrocarbyl substituted phenylenediamine, (2) an aldehyde or ketone and (3) an aliphatic amine at temperatures varying from ambient or about 50° C. to about 250° C. or reflux and pressure varying from atmospheric or slightly higher in molar, less than molar or greater than molar quantites of (1), (2), and/or (3).

30. The product of claim 29 where (1) the phenylenediamine has the following generalized structure:

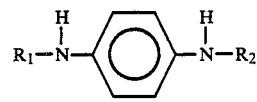

(2) the aldehyde or ketone has the following generalized structure:

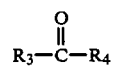

and (3) the aliphatic amine has the following generalized structure:

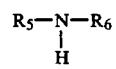

where $R_1$, $R_2$, $R_3$, $R_4$, $R_5$, $R_6$ are hydrogen or $C_1$ to $C_{60}$ hydrocarbyl, or oxygen, sulfur, nitrogen containing $C_2$ to about $C_{60}$ hydrocarbyl.

31. The product of claim 30 where said product has the following generalized structure:

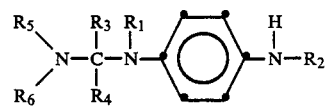

where $R_1$, $R_2$, $R_3$, $R_4$, $R_5$, $R_6$ are hydrogen or $C_1$ to $C_{60}$ hydrocarbyl, or oxygen, sulfur, nitrogen containing $C_2$ to about $C_{60}$ hydrocarbyl.

32. The product of claim 30 where said product has the following generalized structure:

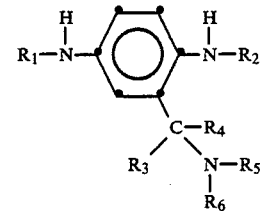

where $R_1$, $R_2$, $R_3$, $R_4$, $R_5$, $R_6$ are hydrogen or $C_1$ to $C_{60}$ hydrocarbyl, or oxygen, sulfur, nitrogen containing $C_2$ to about $C_{60}$ hydrocarbyl.

33. The product of claim 30 where said product has the following generalized structure:

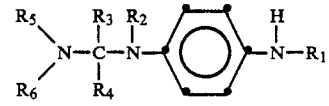

where $R_1$, $R_2$, $R_3$, $R_4$, $R_5$, $R_6$ are hydrogen or $C_1$ to $C_{60}$ hydrocarbyl, or oxygen, sulfur, nitrogen containing $C_2$ to about $C_{60}$ hydrocarbyl.

34. The product of claim 25 where said product has the following generalized structure:

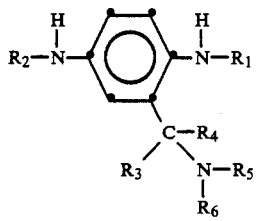

where $R_1$, $R_2$, $R_3$, $R_4$, $R_5$, $R_6$ are hydrogen or $C_1$ to $C_{60}$ hydrocarbyl, or oxygen, sulfur, nitrogen containing $C_2$ to about $C_{60}$ hydrocarbyl.

35. The product of claim 30 where product has the following generalized structure:

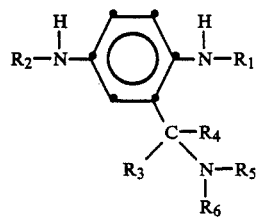

where $R_1$, $R_2$, $R_3$, $R_4$, $R_5$ and $R_6$ are hydrogen or $C_1$ to about $C_{60}$ hydrocarbyl.

36. The product of claim 29 where the phenylenediamine is selected from the group consisting of mono- and di-substituted para-phenylenediamines, mono- and di-substitutes meta-phenylenediamines, and mono- and di-substituted ortho phenylenediamines.

37. The product of claim 36 where the phenylenediamine has the following generalized structure:

where $R_7$ is $C_1$ to about $C_{60}$ hydrocarbyl or oxygen, sulfur, nitrogen containing $C_2$ to about $C_{60}$ hydrocarbyl.

38. The product of claim 36 where the phenylenediamine has the following generalized structure:

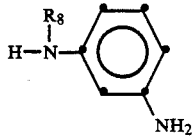

where $R_8$ is $C_1$ to about $C_{60}$ hydrocarbyl or oxygen, sulfur, nitrogen containing $C_2$ to about $C_{60}$ hydrocarbyl.

39. The product of claim 36 where the phenylenediamine has the following generalized structure:

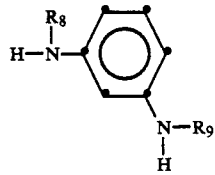

where $R_8$ is $C_1$ to about $C_{60}$ hydrocarbyl or oxygen, sulfur, nitrogen containing $C_2$ to about $C_{60}$ hydrocarbyl.

40. The product of claim 36 where the phenylenediamine has the following generalized structure:

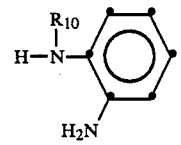

where $R_{10}$ is $C_1$ to about $C_{60}$ hydrocarbyl or oxygen, sulfur, nitrogen containing $C_2$ to about $C_{60}$ hydrocarbyl.

41. The product of claim 36 where the phenylenediamine has the following generalized structure:

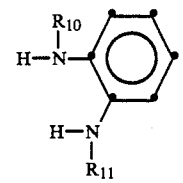

where $R_{10}$ and $R_{11}$ are $C_1$ to about $C_{60}$ hydrocarbyl or oxygen, sulfur, nitrogen containing $C_2$ to about $C_{60}$ hydrocarbyl.

42. The product of claim 29 where the reactants are a mixture of $C_{11}$–$C_{14}$ tertiary-alkyl amines, N,N'-bis(1,4-dimethylpentyl) para-phenylenediamine and paraformaldehyde.

43. The product of claim 20 where the reactants are a mixture of diethanol amine, N,N'-bis(1,4-dimethylpentyl) paraphenylenediamine and 2-ethylhexanal.

44. The product of claim 29 where the reactants are a mixture of bis(2-ethylhexyl) amine, formaldehyde and N,N'-bis(1,4-dimethylphentyl) para-phenylenediamine.

45. The product of claim 29 where the reactants are a mixture of a polyether amine, formaldehyde and N,N'-di-sec-butyl-para-phenylenediamine.

46. The product of claim 45 wherein the polyether amine is selected from polyoxyalkyleneamines, polyoxyalkylenediamines and polyoxyalkylenetriamines.

47. The product of claim 46 wherein the polyether amine is selected from propylene oxide, ethylene oxide and/or mixed propylene oxide, ethylene oxide based polyether amines.

48. The product of claim 47 where the polyether amine is a primary polyether amine derived from nonylphenol, ethylene oxide and propylene oxide.

49. The product of claim 48 wherein the polyether amine is Surfonamine MNPA.

50. A process of preparing an addive product of reaction comprising reacting (1) a N,N'-dihydrocarbyl substituted phenylenediamine (2) an aldehyde or ketone and (3) an aliphatic amine, in less than molar, molar or more than molar quantities of amine or diamine at temperatures varying from ambient to about 250° C. or reflux, at pressures varying from about ambient to slightly higher for a time sufficient varying from 0.5 to 12 hours or more.

51. The process of claim 50 where the phenylenediamine is selected from the group consisting of mono- and di-substituted para-phenylenediamines, mono- and di-substituted meta-phenylenediamines, and mono- and di-substituted ortho-phenylenediamines.

52. The process of claim 50 where the phenylene diamine has the following generalized structure:

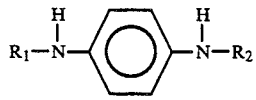

where R and R₂ are hydrogen or $C_1$ to $C_{60}$ hydrocarbyl, or oxygen, sulfur, nitrogen containing $C_2$ to about $C_{60}$ hydrocarbyl.

53. The process of claim 50 where the aldehyde or ketone has the following generalized structure:

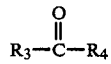

where $R_3$ and $R_4$ are hydrogen or $C_1$ to $C_{60}$ hydrocarbyl, or oxygen, sulfur, nitrogen containing $C_2$ to about $C_{60}$ hydrocarbyl.

54. The process of claim 50 where the alphatic amine has the following generalized structure:

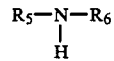

where $R_5$ and $R_6$ are hydrogen or $C_1$ to $C_{60}$ hydrocarbyl, or oxygen, sulfur, nitrogen containing $C_2$ to about $C_{60}$ hydrocarbyl.

55. The process of claim 50 where the reactants are are a mixture of $C_{11}$–$C_{14}$ tertiary-alkyl amines, N,N'-bis(1,4-dimethylpentyl) para-phenylenediamine and paraformaldehyde.

56. The process of claim 50 where the reactants are a mixture of diethanol amine, N,N'-bis(1,4-dimethylpentyl) para-phenylenediamine and 2-ethylhexanal.

57. The process of claim 50 where the reactants are a mixture of bis(2-ethylhexyl) amine, formaldehyde and N,N'-bis(1,4-dimethylphentyl) para-phenylenediamine.

58. The process of claim 50 where the reactants are a mixture of a polyether amine, formaldehyde and N,N'-di-sec-butyl-para-phenylenediamine.

59. A method for improving the antioxidant characteristics of a lubricant composition and comprising adding from about 0.001 to about 10 weight percent of a product of reaction as described in claim 29 to an oil of lubricating viscosity or grease or other solid lubricant prepared therefrom.

60. A method of improving the fuel economy of an internal combustion engine comprising contacting/treating the moving parts thereof with a composition as described in claim 1.

* * * * *